US006617307B1

(12) United States Patent
Nishimura et al.

(10) Patent No.: US 6,617,307 B1
(45) Date of Patent: Sep. 9, 2003

(54) PEPTIDE AND OSTEOGENETIC ACCELERATOR

(75) Inventors: Yoshihiko Nishimura, 25, Kitashirakawa Nishisenouchi-cho, Sakyo-ku, Kyoto-shi, Kyoto 606-8255 (JP); Yoshihisa Suzuki, 38-4-301, Kitashirakawa Oiwake-cho, Sakyo-ku, Kyoto-shi, Kyoto 606-8224 (JP); Masao Tanihara, A-206, 8916-5, Takayama-cho, Ikoma-shi, Nara 630-0101 (JP)

(73) Assignees: Kyocera Corporation, Kyoto (JP); Yoshihisa Suzuki, Kyoto (JP); Yoshihiko Nishimura, Kyoto (JP); Masao Tanihara, Nara (JP)

( * ) Notice: Subject to any disclaimer, the term of this patent is extended or adjusted under 35 U.S.C. 154(b) by 0 days.

(21) Appl. No.: 09/439,779

(22) Filed: Nov. 12, 1999

(30) Foreign Application Priority Data

Nov. 12, 1998 (JP) .......................................... 10-322075

(51) Int. Cl.[7] .......................... A61K 38/03; C07K 4/00; C07K 14/51
(52) U.S. Cl. ......................... 514/13; 530/326; 530/334; 530/344; 424/422; 424/423; 424/426; 523/115
(58) Field of Search ........................... 514/13; 530/326, 530/334, 344; 424/422, 423, 426; 523/115

(56) References Cited

FOREIGN PATENT DOCUMENTS

| EP | 99402815 | 9/2000 |
|---|---|---|
| JP | 06/296677 | 10/1994 |
| JP | 07/088174 | 4/1995 |
| JP | 07/116240 | 9/1995 |
| JP | 07/246235 | 9/1995 |
| JP | 10/070989 | 3/1998 |
| JP | 10/151188 | 6/1998 |
| WO | WO 89/09787 | 10/1989 |
| WO | WO 89/09788 | * 10/1989 |

OTHER PUBLICATIONS

Database Biosis 'Online! Biosciences Information Service Philadelphia, PA, US: R. Bellamkonda, et al.: "Laminin oligopeptide derivatized agarose gels allow three–dimensional neurite extension in vitro" XP002145150 & J. Neuroscience Research, 1995, vol. 41, pp. 501–509.

T.J. Gao, et al.: "Bone inductive potential and dose–dependent response of bovine bone morphogenetic protein combined with type IV collagen carrier" Annales Chirurgiae et Gynaecologiae, vol. 82, 1993, pp. 77–84.

S. Ijiri, et al., : "Ectopic bone induction in porous apatite–wollastonite–containing glass ceramic combined with bone morphogenetic protein" J. Biomed. Mater. Res., vol. 35, No. 4, Jun. 15, 1997 pp. 421–432.

Novel Regulators of Bone Formation: Molecular Clones and Activities; Wozney, et al. / Science, vol. 242: Research Articles, pp. 1528–1534 / Dec. 16, 1988.

"Recombinant human bone morphogenetic protein induces bone formation"; Wang, et al.; Proc. Natl. Acad.: Sci. USA, vol. 87, pp. 2220–2224, Mar. 1990, Biochemistry.

* cited by examiner

*Primary Examiner*—Christopher S. F. Low
*Assistant Examiner*—Chih-Min Kam
(74) *Attorney, Agent, or Firm*—Hogan & Hartson, LLP

(57) ABSTRACT

A peptide has any one of the sequences SEQ ID NO.1 to SEQ ID NO.8, or has a sequence derived from any one of the sequences SEQ ID NO.1 to SEQ ID NO.8 by substitution, deletion or addition of one or several amino acids therein and having an osteogenetic activity.

30 Claims, No Drawings

PEPTIDE AND OSTEOGENETIC ACCELERATOR

CROSS-REFERENCE TO RELATED APPLICATION

This application is related to Japanese application No. HEI 10(1998)-322075 filed on Nov. 12, 1998, whose priority is claimed under 35 USC §119, the disclosure of which is incorporated by reference in its entirety.

BACKGROUND OF THE INVENTION

1. Field of the Invention

The present invention relates to a novel peptide having osteogenetic activity and an osteogenetic accelerator containing the same as an active ingredient.

The peptide of the present invention, which has the osteogenetic activity, is useful for treatment of fractures, as a filler in deficient sites of bone, for inhibition of decrease in bone substance related to osteoporosis and periodontic diseases, for prevention of fractures associated with osteoporosis and rheumatoid arthritis and the like.

2. Description of Related Art

Bone morphogenetic protein (BMP) is a member of transforming growth factor (TGF) β family (Wozney, J. M. et al, Science, 242, 1528 (1988)), and its active form exists as a homodimer having a molecular weight of about 18kD. BMP has the function of acting on undifferentiated mesenchymal cells, inducing differentiation to chondroblasts and osteoblasts and effecting chondrogenesis and osteogenesis (Wang, E. A. et al. Proc. Natl. Acad. Sci. USA, 87, 2220 (1990)).

For this reason, BMP is expected to be effective in treatment of fractures, inhibition of decrease in the bone substance related to osteoporosis and periodontic diseases, in prevention of fractures associated with osteoporosis and rheumatoid arthritis and the like (for example, see Japanese Unexamined Patent Publications Nos. HEI 6(1994)-298800 and HEI 10(1998)-70989).

Also, there are known a number of inventions relating to implants and compositions in which BMP is combined with a variety of matrices (for example, see Japanese Unexamined Patent Publications Nos. HEI 6(1994)-296677, HEI7 (1995)-246235, HEI 7(1995)-116240, HEI 7(1995)-88174 and HEI 10(1998)-151188).

However, the above-described BMP, when it is administered in vivo, disappears from blood within a few minutes and loses its effect. If administered in a large amount for compensating that, BMP might possibly cause various adverse effects, including toxic effects on livers and kidneys. Further, BMP has an immunogenicity because of its large molecular weight, and might possibly cause anaphylactic shock when administered repeatedly. furthermore, where BMP is impregnated in matrices of decalcificated bone or collagen for use, osteogenetic activity is expressed, but there may be another problem of antigenicity or infection attributed to the matrices.

SUMMARY OF THE INVENTION

Under these circumstances, an object of the present invention is to provide a peptide having an osteogenetic activity in which peptide the above-mentioned problems are alleviated, and an osteogenetic accelerator containing the peptide.

According to the present invention, the above-mentioned object is achieved by a peptide having any one of the sequences SEQ ID NO.1 to SEQ ID NO.8.

Also the object of the present invention is achieved by an osteogenetic accelerator containing the above-mentioned peptide.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

The peptides of the present invention are not necessarily required to have exactly the same amino acid sequence as represented by any one of SEQ ID NO.1 to SEQ ID NO.8, provided that they have the osteogenetic activity. In other words, so long as the peptides have the osteogenetic activity, one to several amino acids in the sequences may optionally be deleted or substituted or one to several amino acids may optionally be added to the sequences, by a usual technique in genetic engineering or in peptide synthesis. The optionally deleted, substituted or added amino acids may be selected as appropriate depending on the kind of amino acids, a site and the like.

In the present invention, to "have the osteogenetic activity" may be construed as activity of accelerating the activation of alkaline phosphatase in osteoblasts (Yamaguchi, A., Molecular Medicine, Vol.30, No.10, 1232(1993)) so as to form neogenetic bone or induce growth of existing bone.

In the present specification, amino acid residues are represented by abbreviatory symbols as follows:

Ala: L-alanine residue
Asn: L-asparagine residue
Cys: L-cysteine residue
Gln: L-glutamine residue
Glu: L-glutamic acid residue
Ile: L-isoleucine residue
Leu: L-leucine residue
Lys: L-lysine residue
Pro: L-proline residue
Ser: L-serine residue
Thr: L-threonine residue
Val: L-valine residue
Glx: L-L-glutamine residue or L-glutamic acid residue
Xaa: amino acid defined in each sequence Also in the present specification, the amino acid sequence of a peptide is written according to the conventional notation, with an amino group at the N-terminal appearing on the left hand of the sequence and carboxyl group at the C-terminal appearing on the right hand thereof.

The amino acid sequences represented by SEQ ID NO.1 to SEQ ID NO.8 may also be represented by the formula:

—Y1-Asn-Y2-Y3-Y4-Pro-Lys-Y5-Cys-Cys-Y6-Pro-Thr-Y7-Leu-Y8-Ala-Y9—, wherein Y1 is a peptide residue or an amino acid residue selected from the group consisting of Asn-Ser-Val and Ile, Y2 is an amino acid residue or a peptide residue selected from the group consisting of Ser and Pro-Glu, Y3 is an amino acid residue selected from the group consisting of Lys, Ser and Thr, Y4 is an amino acid residue selected from the group consisting of Ile and Val, Y5 is an amino acid residue selected from the group consisting of Ala and Pro, Y6 is an amino acid residue selected from the group consisting of Ala and Val, Y7 is an amino acid residue selected from the group consisting of Glu and Gln, Y8 is an amino acid residue selected from the group consisting of Ser and Asn, Y9 is an amino acid residue or a peptide residue selected from the group consisting of Ile and Ile-Ser.

The peptides of the present invention may be produced by a method usually used for synthesizing peptides, for example, by a solid phase synthesis method or by a liquid phase synthesis method. The solid phase synthesis method is simpler in operation (for example, see "Sequel to Biochemical Experiments 2, Chemistry about Protein (the second volume)" p.p.641–694 edited by the Biochemical Society in Japan published on May 20, 1987 by Tokyo Kagaku Dojin, Japan and "Solid Phase Peptide Synthesis—A Practical Method" p.p.152–154by Atherton, E. et al. published in 1989 by IRL Press, Oxford). The solid phase synthesis can be carried out usually by protecting amino groups with appropriate protecting groups, for example, either Boc (tert-butoxycarbonyl) or Fmoc (9-fluorenylmethyloxycarbonyl), or a combination thereof.

For producing the peptide of the present invention, for example, 1) an amino acid corresponding to the C-terminal of the peptide to be produced is bonded to a solid phase material insoluble to a reaction solvent via an α-COOH group of the amino acid; 2) subsequently, in the direction to the N-terminal of the peptide, a corresponding amino acid or peptide fragment is bonded by condensation to the amino acid of 1) after protecting other functional groups such as an α-amino group of the corresponding amino acid or peptide fragment other than an α-COOH group; 3) a protecting group of an amino group forming a peptide bond such as an α-amino group is removed from the bonded amino acid or peptide fragment; these steps are repeated to elongate a peptide chain in order to form a peptide chain corresponding to the desired peptide.

The thus produced peptide chain is detached from the solid phase material and protecting groups are removed from protected functional groups. Subsequently the peptide chain is purified, thereby to obtain the desired peptide.

Here, as the solid phase material, styrene-divinyl benzene copolymers, Merrifield resins, chloromethyl resins, Wang resins, Sieber resins, rink amide resins, rink acid resins, 2-chlorotrityl chloride resins, HMBA-MBHA resins, MBHA resins, oxime resins and the like may be used. Among these resins, styrene-divinyl benzene copolymers are preferred.

It is preferred from the viewpoint of preventing side reaction that the detachment of the peptide chain from the solid phase material and the removal of the protecting groups are carried out simultaneously using trifluoroacetic acid or hydrogen fluoride.

As a solvent and a condensing agent in the peptide synthesis, any ones usually known in the art may be used as required. For example, DMF (dimethylformamide), trichloroethanol, N-methylpyrrolidone and the like may be mentioned as solvents, and DCC, HATU (0-(7-azabenzotriazole-1-yl)-1,1,3,3-tetramethyl uronium hexafluorophosphate), HOBt (1-hydroxybenzotriazole), HBTU (0-benzotriazole-1-yl-N,N,N',N'-tetramethyl uronium hexafluorophosphate), PyBOP (benzotriazole-1-yl-oxy-tris-pyrrolidinophosphonium hexafluorophosphate), $CF_3$-$NO_2$-PyBOP and the like may be mentioned as condensing agents.

For purifying the obtained peptide, it is effective to utilize reverse phase liquid chromatography.

Either or both of the N- and C-terminals of the peptide of the present invention may optionally be modified chemically. For example, the N-terminal may be acetylated and the C-terminal may be amidated.

The peptide of the present invention may form a physiologically acceptable salt by conventional salt formation reaction. Such salts can include salts with inorganic acids such as hydrochloric acid, sulfuric acid and phosphoric acid; salts with organic acids such as lactic acid, tartaric acid, maleic acid, fumaric acid, oxalic acid, malic acid, citric acid, oleic acid and palmitic acid; salts with hydroxides and carbonates of alkali metals and alkali earth metals such as sodium, potassium, calcium and aluminum; and salts with amines such as triethylamine, benzylamine, diethanolamine, t-butylamine, dicyclohexylamine and arginine.

Preferred examples of peptides provided by the present invention are peptides having amino acid sequences represented by SEQ ID NO.9 or SEQ ID NO.10, which are examples of SEQ ID NO.1 and peptides having an amino acid sequence represented by SEQ ID NO. 11, which is an example of SEQ ID NO.8, and particularly peptides having amino acid sequences represented by SEQ ID NO. 9 to SEQ ID NO.11 and having an amino group at the N-terminal and a carboxyl group at the C-terminal, and peptides having an amino acid sequence represented by SEQ ID NO.9 and having an acetyl group at the N-terminal and a carboxyl group at the C-terminal.

These peptides may have a part of thereof deleted or substituted or have addition to amino acid(s) thereto so long as they have the osteogenetic activity, as described above.

It is verified that the peptide of the present invention has the osteogenetic activity and is negligible in toxicity such as cytotoxity, systemic acute toxicity and the like. As for the osteogenetic accelerator comprised of the peptide of the present invention, it is possible to avoid the problems of infection and antigenicity resulting from matrices by means of sterilizing operation such as γ-ray sterilization, moist heat vapor sterilization and selection of a carrier made of a polysaccharide having low antigenicity or the like during production process.

The peptide of the present invention may be used singly for the purpose of preventing or treating bone fractures. Also the peptide may be used in the form of an osteogenetic accelerator obtained by fixing, mixing, solving or suspending the peptide in a proper carrier or an aqueous solvent which can contain a variety of pharmacologically acceptable additives such as a stabilizer, a preservative, a thickener, a solubilizer and the like. It is particularly preferable that the osteogenetic accelerator of the present invention is one in which the peptide is fixed to a carrier.

The carrier for fixing the peptide of the present invention is not particularly limited to any type provided that it has compatibility to living bodies. For example, it is possible to use, singly or in combination, carriers which can be degraded and absorbed in vivo, such as covalently crosslinked gels of alginate (Suzuki,Y. et al., J. Biomed. Mater. Res., 39, 317(1998)), gels of protein such as collagen, hyaluronic acid, calcium sulfate, polylactic acid, polyglycolic acid, hydroxyapatite, tricalcium phosphate and the like, as well as various ceramics and artificial bone. In addition, starch gel, chitin/chitosan gel, agarose gel and dextran gel may be used as polysaccharide gels. Among these carriers, a covalently crosslinked gel of alginate and a gel of hyaluronic acid are preferred from the view point of non-inflammatory (J.Biomed.Mater.Res.Appl.Biomater., 48, 522–527 (1999) and J.Artif.Organs, 1, 28–32 (1998)) and non-immunogenic (J.Biomed.Master.Res., 1994, Sep;28 (9):1037–46) properties.

The method of fixing the peptide on a carrier is not particularly limited. It is possible to adopt a fixation method allowing formation of covalent bond, ionic bond, hydrophobic bond, hydrogen bond, SS bond or the like, for example, an immersion, impregnation, spray, application and dropping method with use of a solution containing the peptide. Among these fixation methods, fixation by covalent bond is preferred from the viewpoint of stability and continuity of effect. Such fixation can be done by a method usually used for fixing a physiologically active protein such as an enzyme (for example, see Scouten, W. H., Methods in Enzymol., 135, Mosbach, K. Ed., 1987, Academic Press NY, p.p.30–65).

Preferably, the peptide to be fixed is used in an amount of about 0.01 to about 50 parts by weight, preferably about 0.1 to 25 parts by weight, with respect to 100 parts by weight of a dry carrier. The peptide thus fixed is usually used for treatment of a fracture or the like by being implanted in a deficient site in bone. If the peptide is used in an amount smaller than 0.01 parts by weight with respect to 100 parts by weight of a dry carrier, the effect of the peptide tends to be insufficient. If the peptide is used in an amount larger than 50 parts by weight, on the other hand, the ratio of fixation of the peptide to the carrier declines and the peptide tends not to be utilized effectively.

As aqueous solvents, physiological saline and physiologically acceptable aqueous solutions of mannitol, sucrose, lactose, maltose, glucose, fructose or the like. A glucose aqueous solution of 5% and a physiological saline are preferable. These aqueous solvents may be used so that the concentration of the peptide is 0.001% to 5%, preferably 0.01% to 1%. If the concentration of the peptide exceeds 5%, the viscosity of the solution rises. Accordingly, there are tendencies that administration becomes difficult and that the peptide separates at an administration site and as a result its effect declines. If the concentration of the peptide is below 0.001%, on the other hand, the effect of the peptide tends to be insufficient.

The osteogenetic accelerator may be used by intravenous, subcutaneous, intraperitoneal, intra-articular or dermal administration or by filling it in a defective site in bone. Further, if capsulated or made into liposomes by the conventional method, the osteogenetic accelerator can be administered orally.

Thus, the peptide and the osteogenetic accelerator of the invention can promote treatment of fractures by being administered to patients with fractures caused by rheumatoid arthritis and osteoporosis or by being filled or implanted in a defective site in bone. Also they can inhibit decrease in bone substance and prevent fractures by being administered to patients with rheumatoid arthritis, osteoporosis and periodontic diseases.

The dose of the peptide as an active ingredient may vary as required depending upon the weight of bone desired to be formed, the site of injured bone, the condition of bone, and the age, sex and weight of a patient and the like. But usually, the peptide expresses its effect by being administered at a dose of 0.01 µg/kg to 33 mg/kg (for an adult), preferably 0.01 µg/kg to 3.3 mg/kg (for an adult), once per day.

EXAMPLES

The present invention is now described by way of examples, which should not be construed to limit the scope of the invention.

Example 1

A peptide having the amino acid sequence of SEQ ID NO. 9 which had an amino group at the N-terminal and a carboxyl group at the C-terminal was synthesized by the solid phase synthesis method using an automatic peptide synthesizer.

More particularly, with use of 0.1 mmol of particulate resin (produced by US Applied Biosystems, HMP isoleucine) comprised of styrene-divinylbenzene copolymer (the molar composition ratio of styrene to divinylbenzene was 99:1) containing 4-($N^\alpha$-9-(fluorenylmethoxycarbonyl)-L-isoleucyl)-oxymethyl-phenoxy-methyl group in a proportion of 0.65 mmol/g-resin, successively bonded were amino acids corresponding in the direction from the carboxyl terminal to the amino terminal of the peptide.

In bonding reaction, used as amino acids were $N^\alpha$-9-(fluorenylmethoxycarbonyl)-$N^\beta$-trityl-L-asparagine (Fmoc asparagine), $N^\alpha$-9-(fluorenylmethoxycarbonyl)-0-t-butyl-L-serine (Fmoc serine), $N^\alpha$-9-(fluorenylmethoxycarbonyl)-valine (Fmoc-valine), $N^\alpha$-9-(fluorenylmethoxycarbonyl)-$N^\epsilon$-t-butyloxycarbonyl-L-lysine (Fmoc lysine), $N^\alpha$-(fluorenylmethoxycarbonyl)-L-isoleucine (Fmoc isoleucine), $N^\alpha$-(fluorenylmethoxycarbonyl)-L-proline (Fmoc proline), $N^\alpha$-(fluorenylmethoxycarbonyl)-L-alanine (Fmoc Alanine), $N^\alpha$-9-(fluorenylmethoxycarbonyl)-S-trityl-L-cysteine (Fmoc cysteine), $N^\alpha$-9-(fluorenylmethoxycarbonyl)-0-t-butyl-L-threonine (Fmoc threonine), $N^\alpha$-9-(fluorenylmethoxycarbonyl)-$\gamma$-butyl-L-glutamic acid (Fmoc glutamic acid), and $N^\alpha$-(fluorenylmethoxycarbonyl)-L-leucine (Fmoc leucine), all being produced by US applied Biosystems, in the amount of 1 mmol in each bonding step.

As the condensing agent and additive for peptide synthesis, HBTU and HOBt were used.

The resulting peptide resin was treated with 10 ml of trifluoroacetic acid containing 2.5% of water and 2.5% of ethanedithiol for three hours. The resulting solution was added to diethyl ether. The generated precipitate was further washed with diethyl ether several times in order to deprotect the peptide and detach it from the resin. The resulting crude product was purified by preparative RP-HPLC (column: Novapak HR C18 25×100 mm, RCM 25×10 with a pressure module produced by Nippon Waters Kabushiki Kaisha, Japan) using a mixture solvent of water and acetonitrile (with varying the concentration of acetonitrile from 5 vol % to 50 vol % in 30 minutes) containing trifluoroacetic acid in the proportion of 0.05%.

The resulting purified peptide was subjected to an AKTA explorer 1OXT produced by Pharmacia Biotech Kabushiki Kaisha, Japan (column : µRPC C2/C18 ST4.6/100 produced by Pharmacia Biotech Kabushiki Kaisha, mobile phase: a mixture solvent of water and acetonitrile containing 0.05 vol % of trifluoroacetic acid (with varying the concentration of acetonitrile from 5 vol % to 50 vol % in 30 minutes), a flow rate: 0.5 ml/min.). A single peak was observed at 24.5 min.

The molecular weight of the purified peptide was found to be 2,075 by FAB mass spectrometry (theoretical molecular weight : 2,074.45). Therefore, it was verified that the desired peptide was obtained.

Examples 2 to 4

A peptide (Example 2) having the amino acid sequence of SEQ ID NO. 9 and having an acetyl group at the N-terminal and a carboxyl group at the C-terminal, a peptide (Example 3) having the sequence of SEQ ID NO. 10 and having an amino group at the N-terminal and a carboxyl group at the C-terminal, and a peptide (Example 4) having the sequence of SEQ ID NO. 11 which had an amino group at the N-terminal and a carboxyl group at the C-terminal were synthesized in the same manner as in Example 1.

In Example 2, a peptide resin obtained by the automatic peptide synthesizer was suspended in 20 ml of dimethylformamide with stirring, to which 2 ml of acetic anhydride and 26 μl of diisopropylethylamine were added, followed by stirring at room temperature for another four hours. The acetylated peptide resin was well washed on a glass filter with methanol, and then dried under reduced pressure.

In Example 4, used was 0.1 mmol of particulate resin (produced by US Applied Biosystems, HMP serine) comprised of styrene-divinylbenzene copolymer (the molar composition ratio of styrene to divinylbenzene was 99 1) containing 4-($N^\alpha$-9-(fluorenylmethoxycarbonyl)-0-t-butyl-L-serin)-oxy methyl-phenoxy-methyl group in a proportion of 0.65 mmol/g-resin.

As an amino acid, used was $N^\alpha$-9-(fluorenylmethoxycarbonyl)-$N^\gamma$-trityl-L-glutamine (Fmoc glutamine) produced by US Applied Biosystems in addition to the amino acids used in Example 1.

The resulting peptide resins were subjected to deprotection and detachment from the solid phase and the resulting crude products were purified, in the same manner as in Example 1. The purified peptides were each examined on elution time and molecular weight by analytical HPLC and by FAB mass spectroscopy. The results are shown in Table 1.

TABLE 1

| Examples | Elution Time | Molecular Weight | Theoretical Molecular Weight |
| --- | --- | --- | --- |
| Example 2 | 25.2 min | 2117 | 2116.49 |
| Example 3 | 25.0 min | 2033 | 2033.36 |
| Example 4 | 22.1 min | 2097 | 2096.46 |

Test Example 1

Determination of Alkali Phosphatase Activity in Bone Marrow Cells of Rats—in Vitro Femurs were aseptically taken out of six-week-old female rats (Lewis, purchased from Nippon SLC). Both ends of the femurs were cut off. Then bone marrow was extruded into centrifugal tubes by means of Eagle's MEM containing 10% of fetal bovine serum using an injection syringe with a 21G injection needle. The bone marrow cells were sufficiently dispersed with a pipette and filtered by a 40 μm filter to remove agglutinations. The resulting bone marrow cells were centrifuged with Eagle's MEM containing 10% of fetal bovine serum three times (1200 rpm, 5 min.×3), and then the number of cells was counted. The bone marrow cells were diluted with Alpha MEM containing 10% of fetal bovine serum so that relatively large bone marrow cells were present in a concentration of $10^6$/ml. The dilution was pipetted 10 ml in each culture flask having a culture area of 25 cm$^2$ and incubated at 37° C. in the presence of 5% $CO_2$.

Twenty-four hours after the incubation was started, medium was replaced with Alpha MEM containing 10% of fetal bovine serum and the peptide obtained in Example 1. Thereafter, the medium was replaced similarly every three days.

One week after the incubation was started, multiplied cells were stained with an alkaline phosphatase staining kit (produced by Sigma).

The results showed remarkable increase in the alkaline phosphatase activity as compared with cases where human IL-1 was added in a concentration of 10 ng/ml instead of the peptide obtained in Example 1 and with cases where nothing was added instead of the peptide obtained in Example 1.

The same test was carried out on the peptides obtained in Examples 2 to 4, and as a result, remarkable increase in the alkaline phosphatase activity was observed as in the case of the peptide of Example 1.

Test Example 2

Determination of Alkaline Phosphatase Activity in Bone Marrow Cells of Rats—in Vivo A solution of 500 μg of the peptide obtained in Example 1 in phosphate buffer (PBS: 10 mM, containing 0.15M of sodium chloride, pH: 7.4) was intraperitoneally administered to six-week-old female rats (purchased from Nippon SLC, Japan) three times in a week. After one week, femurs of the rats were taken out aseptically. Both ends of the femurs were cut off. Then bone marrow was extruded into centrifugal tubes by means of Eagle—MEM containing 10% of fetal bovine serum using an injection syringe with a 21G injection needle. The bone marrow cells were sufficiently dispersed with a pipette and filtered by a 40 μm filter to remove agglutinations. The resulting bone marrow cells were centrifuged with Eagle's MEM containing 10% of fetal bovine serum three times (1200 rpm, 5 min.×3), and then the number of cells was counted. The bone marrow was diluted with Alpha MEM containing 10% of fetal bovine serum so that relatively large bone marrow cells were present in a concentration of $10^6$/ml. The dilution was pipetted on a 24-hole culture plate, 1 ml per well, and incubated at 37° C. in the presence of 5% $CO_2$.

Twenty-four hours after the incubation was started, medium was replaced with Alpha MEM containing 10% of fetal bovine serum. Thereafter, the medium was replaced similarly every three days.

One week after the incubation was started, the culture plate was cleared of supernatant and washed with PBS once. In each well of the 24-well plate, 1 ml of Tris buffer (20 mM, pH 8.5) containing 1% Triton X-100 was added and allowed to stand for 30 minutes to dissolve cells.

With respect to 100 μl of the resulting cell solution, 100 μl of Tris buffer (1.5 M, containing 1 mM of $ZnCl_2$ and 1 mM of $MgCl_2$, pH 8.5) containing 7.5 mM of p-nitrophenyl phosphate were added. Increase in absorbency at 405 nm was measured to determine the alkaline phosphatase activity in the cell solution. The concentration of protein in the cell solution was also determined using a BCA assay kit (produced by Pierce).

As a result, the alkaline phosphatase activity in the rats having been administered the peptide of Example 1 was 6.3±1.4 μmol/min.mg-protein, while that in rats having received administration only of PBS instead of the peptide of Example 1 was 3.2±1.1 μmol/min.mg-protein. It was found that the peptide of Example 1 brought about remarkable increase in the alkaline phosphatase activity.

Example 5

Ethylene diamine (EDA, produced by Wako Jun'yaku Kogyo Kabushiki Kaisha, Japan), 0.6 g (10mmol), dissolved in 10 ml of methanol was dropped into 150 ml of methanol in which 2.3 g (20 mmol) of N-hydroxysuccinimide (HOSu, produced by KK Peptide Kenkyusho, Japan) had been dissolved, while stirring at room temperature. After dropping, the mixture was stirred for another one hour. Precipitated crystals were taken by filtration and dried under reduced pressure, to obtain 2.6 g (a yield of about 90%) of ethylenediamine 2N-hydroxysuccinimide salt (EDA.2HOSu).

EDA. 2HOSu, 66 mg, and 1-ethyl-3-(3-dimethylaminopropyl)-carbodiimide hydrochloride (WSCD.HCl, produced by KK Peptide Kenkyusho), 0.48g, were dissolved in 30 ml of 1 wt % aqueous solution of sodium alginate (produced by Funakoshi Kabushiki Kaisha, viscosity: 550 cp, M/G ratio: 1.0). The resulting mixture was cast on a 10 cm×10cm Teflon-coated aluminum tray and allowed to stand at 25° C. for 48 hours, to obtain a covalently crosslinked gel of alginate.

The gel was sufficiently washed with a purified water for injection (produced by Otsuka Seiyaku) in which 2.5 mM of $CaCdl_2$ and 143 mM of NaCl had been dissolved and then washed only with the purified water for injection. The alginate gel after washing was freeze-dried to obtain a white sponge-like gel.

The resulting sponge-like gel, 0.1 g, was immersed in 20 ml of dimethylformamide, to which 12 mg of N-hydroxysuccinimide and 19 mg of WSCD.HCl were added, and shook at room temperature overnight. The sponge-like gel was well washed with methanol and dimethylformamide, to which 10 ml of dimethylformamide solution containing 20 mg of the peptide obtained in Example 1 was added, and shook at room temperature overnight. The resulting gel was well washed with methanol and ethanol, to obtain an osteogenetic accelerator in which the peptide of Example 1 was fixed.

Test Example 3

Intramuscular Implant Test on Rats

The osteogenetic accelerator obtained in Example 5, 0.01 g, was implanted in femoral muscle of six-week-old female SD rats (purchased from Nippon SLC). After three weeks, peripheral tissue including implants was taken out and subjected to tissue staining (see "Clinical Test Techniques" edited by Kanno,T., Matsuda,N., ⑤ Pathology.Pathological Tissue Cytology, published by Igakushoin, Japan in 1991).

As a result, von Kossa staining revealed that calcium deposited on implant sites. For comparison, a sponge-like gel not having the peptide fixed thereon was implanted on the opposite side of the identical rats, where deposition of calcium was not recognized at all through the von Kossa staining.

Test Example 4

Deficient Bone Site Implant Test on Dogs

The osteogenetic accelerator obtained in Example 5, 0.07 g, was implanted in deficient sites of 7 mm diameter which had been artificially formed in mandibles of six-month-old female beagles (purchased from Nippon SLC). Two weeks after implantation, tissue including the implant sites was taken out and subjected to tissue staining. Formation of neogenetic bone was obviously observed. For comparison, a sponge-like gel not having the peptide fixed thereon was implanted on the opposite side of the identical dogs, where any neogenetic bone was not recognized at all.

Test Example 5

Cytotoxicity Test in Vitro—Rat Bone Marrow Cells

Femurs were aseptically taken out of six-week-old female rats (Lewis, purchased from Nippon SLC). Both ends of the femurs were cut off. Then bone marrow was extruded into centrifugal tubes by means of Eagle's MEM containing 10% of fetal bovine serum using an injection syringe with a 21G injection needle. The bone marrow cells were sufficiently dispersed with a pipette and filtered through a 40 μm filter to remove agglutinations. The resulting bone marrow cells were centrifuged with Eagle's MEM containing 10% of fetal bovine serum three times (1200 rpm, 5 min.×3), and then the number of cells was counted. The bone marrow cells were diluted with Alpha MEM containing 10% of fetal bovine serum so that relatively large bone marrow cells were present in a concentration of $10^6$/ml. The dilution was pipetted 10 ml in each culture flask having a culture area of 25 $cm^2$ and incubated at 37° C. in the presence of 5% $CO_2$. To the resulting dilution, a solution of the peptide described in Example 1 in phosphate buffer (PBS: 10 mM, containing 0.15M of sodium chloride, pH: 7.4) was added so that the resulting concentration became 30 μg/ml.

Twenty-four hours after the incubation was started, culture medium was removed and Alpha MEM containing 10% of fetal bovine serum and 30 μg/ml of the peptide described in Example 1 was added to the cells under culture. Thereafter, the medium was replaced similarly every two days. Incubation was continued for seven days. After seven days, the number of formed colonies of bone marrow cells was counted using Giemsa staining. The number of colonies was 101 in average with flasks to which the peptide of Example 1 had been added, and it was 89 in average with flasks to which PBS has been added instead of the peptide of Example 1 in the same amount. The results showed that the peptide of Example 1 did not prevent growth of bone marrow cells and that it did not have cytotoxicity.

Test Example 6

Cytotoxicity Test in Vitro—C3H10T1/2 Cells

C3H10T1/2 cells were dispersed in Eagle's MEM containing 10% fetal bovine serum, pipetted on a 96-well culture plate, 3750 cells per well, and incubated at 37° C. in the presence of 5% $CO_2$. Into the wells, a PBS solution of the peptide described in Example 1 was added so that the resulting concentration became 100 μg/ml, followed by incubation under the same conditions for six days. Then the culture medium was removed and a cytolytic solution (0.1M Tris-HCl buffer containing 1% Triton X-100, pH9) was added to dissolve cells. Then the concentration of protein was determined using BCA reagent (produced by Funakoshi Kabushiki Kaisha).

The concentration of protein was 0.12±0.02 mg/ml (n=12) with wells to which the peptide of Example 1 had been added, and it was 0.07±0.03 mg/ml (n=12) with wells to which PBS has been added instead of the peptide of Example 1 in the same amount. The results showed that the peptide of Example 1 did not prevent growth of C3H10T1/2 cells and that it did not have cytotoxicity.

Test Example 7

Acute Toxicity Test on Rats

A PBS solution of 500 μg of the peptide described in Example 1 was intraperitoneally administered to six-week-old female rats (Lewis, purchased from Nippon SLC) three times in a week. After a week, a group having received administration of the peptide of Example 1 showed an increase in weight of 25±6 g (n=6), and a group having received administration of the same amount of PBS instead of the peptide of Example 1 showed an increase in weight of 23±5 g (n=6). It was not recognized that the administration of the peptide of Example 1 prevented increase in weight. Neither were the rats observed to have a poor coat of fur or any abnormal behavior during the test. Therefore, the peptide of Example 1 showed no significant acute toxicity.

According to the present invention, provided are a peptide having the osteogenetic activity in which various side-effects such as cytotoxity are alleviated and an osteogenetic accelerator containing the peptide as an active ingredient. The peptide and the osteogenetic accelerator are useful for treating fractures, filling defective sites in bone, controlling reduction in bone substance involved with osteoporosis and periodontal diseases and preventing fractions associated with osteoporosis and rheumatoid arthritis.

Free Text for Sequence Listing

Each "Xaa" in SEQ ID NO. 1 to SEQ ID No. 8 in the SEQUENCE LISTING indicates amino acids defined as defined below:

In SEQ ID NO. 1 and SEQ ID NO. 2, Xaa at position 6 represents Lys, Ser or Thr, Xaa at position 7 represents Ile or Val, Xaa at position 10 represents Ala or Pro, Xaa at position 13 represents Ala or Val, and Xaa at position 18 represents Ser or Asn.

In SEQ ID NO. 3 and SEQ ID NO. 4, Xaa at position 7 represents Lys, Ser or Thr, Xaa at position 8 represents Ile or Val, Xaa at position 11 represents Ala or Pro, Xaa at position 14 represents Ala or Val, and Xaa at position 19 represents Ser or Asn.

In SEQ ID NO. 5 and SEQ ID NO. 6, Xaa at position 4 represents Lys, Ser or Thr, Xaa at position 5 represents Ile or Val, Xaa at position 8 represents Ala or Pro, Xaa at position 11 represents Ala or Val, and Xaa at position 16 represents Ser or Asn.

In SEQ ID NO. 7 and SEQ ID NO. 8, Xaa at position 5 represents Lys, Ser or Thr, Xaa at position 6 represents Ile or Val, Xaa at position 9 represents Ala or Pro, Xaa at position 12 represents Ala or Val, and Xaa at position 17 represents Ser or Asn.

What is claimed is:

1. A synthesized peptide consisting of any one of the sequences SEQ ID NO: 1.

2. The synthesized peptide according to claim 1 consisting of any one of the sequences SEQ ID NO:9 and SEQ ID NO: 10.

3. An osteogenetic accelerator comprising the peptide set forth in claim 1, or a pharmalogically acceptable salt thereof, attached to a biocompatible carrier.

4. The osteogenetic accelerator according to claim 3, wherein the carrier is selected from a group consisting of a ceramic, an artificial bone, a covalently cross-linked gel of alginate, and a gel of collagen, hyaluronic acid, calcium sulfate, polylactic acid, polyglycolic acid, hydroxyapatite, tricalcium phosphate, starch, chitin/chitosan, agarose, or dextran.

5. The osteogenetic accelerator according to claim 3 which contains 0.01 to 50 parts by weight of the peptide per 100 parts by weight of the carrier.

6. An osteogenetic accelerator comprising the peptide of claim 1, or a pharmacologically acceptable salt thereof, mixed with, dissolved in, or suspended in aqueous solvent.

7. The osteogenetic accelerator according to claim 6, wherein the aqueous solvent is physiological saline solution or a physiologically acceptable aqueous solution selected from a group consisting of mannitol, sucrose, lactose, maltose, glucose, and fructose.

8. The osteogenetic accelerator according to claim 6 or 7, wherein the concentration of the peptide is 0.001% to 5% with respect to the aqueous solvent.

9. The osteogenetic accelerator as set forth in claim 3 which is used for treating a bone fracture by inducing bone formation at the fracture site or for inhibiting a decrease in bone substance.

10. The peptide of claim 1, wherein the peptide N-terminal is acetylated, or the peptide C-terminal is amidated, or both the N-terminal is acetylated and the C-terminal is amidated.

11. A synthesized peptide consisting of the sequence SEQ ID NO:9.

12. An osteogenetic accelerator comprising the peptide set forth in claim 11, or a pharmacologically acceptable salt thereof, attached to a biocompatible carrier.

13. The osteogenetic accelerator according to claim 12, wherein the carrier is selected from a group consisting of a ceramic, an artificial bone, a covalently cross-linked gel of alginate, and a gel of collagen, hyaluronic acid, calcium sulfate, polylactic acid, polyglycolic acid, hydroxyapatite, tricalcium phosphate, starch, chitin/chitosan, agarose, or dextran.

14. The osteogenetic accelerator according to claim 12 which contains 0.01 to 50 parts by weight of the peptide per 100 parts by weight of the carrier.

15. An osteogenetic accelerator comprising the peptide of claim 11, or a pharmacologically acceptable salt thereof, mixed with, dissolved in, or suspended in aqueous solvent.

16. The osteogenetic accelerator according to claim 15, wherein the aqueous solvent is physiological saline solution or a physiologically acceptable aqueous solution selected from a group consisting of mannitol, sucrose, lactose, maltose, glucose, and fructose.

17. The osteogenetic accelerator according to claim 15 or 16, wherein the concentration of the peptide is 0.001% to 5% with respect to the aqueous solvent.

18. The osteogenetic accelerator as set forth in claim 12 which is used for treating a bone fracture by inducing bone formation at the fracture site or for inhibiting a decrease in bone substance.

19. The peptide of claim 11, wherein the peptide N-terminal is acetylated, or the peptide C-terminal is amidated, or both the N-terminal is acetylated and the C-terminal is amidated.

20. An osteogenetic accelerator comprising a physiologically acceptable salt of the peptide set forth in claim 11.

21. A synthesized peptide consisting of the sequence SEQ ID NO:10.

22. An osteogenetic accelerator comprising the peptide set forth in claim 21, or a pharmacologically acceptable salt thereof, attached to a biocompatible carrier.

23. The osteogenetic accelerator according to claim 22, wherein the carrier is selected from a group consisting of a ceramic, an artificial bone, a covalently cross-linked gel of alginate, and a gel of collagen, hyaluronic acid, calcium sulfate, polylactic acid, polyglycolic acid, hydroxyapatite, tricalcium phosphate, starch, chitin/chitosan, agarose, or dextran.

24. The osteogenetic accelerator according to claim 22 which contains 0.01 to 50 parts by weight of the peptide per 100 parts by weight of the carrier.

25. An osteogenetic accelerator comprising the peptide of claim 21, or a pharmacologically acceptable salt thereof, mixed with, dissolved in, or suspended in aqueous solvent.

26. The osteogenetic accelerator according to claim 25, wherein the aqueous solvent is physiological saline solution or a physiologically acceptable aqueous solution selected from a group consisting of mannitol, sucrose, lactose, maltose, glucose, and fructose.

27. The osteogenetic accelerator according to claim 25 or 26, wherein the concentration of the peptide is 0.001 % to 5% with respect to the aqueous solvent.

28. The osteogenetic accelerator as set forth in claim 22 which is used for treating a bone fracture by inducing bone formation at the fracture site or for inhibiting a decrease in bone substance.

29. The peptide of claim 21, wherein the peptide N-terminal is acetylated, or the peptide C-terminal is amidated, or both the N-terminal is acetylated and the C-terminal is amidated.

30. An osteogenetic accelerator comprising a physiologically acceptable salt of the peptide set forth in claim 21.

* * * * *

UNITED STATES PATENT AND TRADEMARK OFFICE
CERTIFICATE OF CORRECTION

PATENT NO.    : 6,617,307 B1
DATED         : September 30, 2003
INVENTOR(S)   : Werner Reichart and Klaus Ganz It is certified that error appears in the above-identified patent and that said Letters Patent is hereby corrected as shown below:

Column 1,
Line 10, "an,arithmetic" should be changed to -- an arithmetic --

Column 2,
Line 13, "a.total" should be changed to -- a total --
Line 24, "a.coating" should be changed to -- a coating --

Signed and Sealed this

Ninth Day of December, 2003

JAMES E. ROGAN
*Director of the United States Patent and Trademark Office*

SEQUENCE LISTING

```
<160> NUMBER OF SEQ ID NOS: 11

<210> SEQ ID NO 1
<211> LENGTH: 20
<212> TYPE: PRT
<213> ORGANISM: Artificial Sequence
<220> FEATURE:
<223> OTHER INFORMATION: Synthesized peptide
<221> NAME/KEY: MISC_FEATURE
<222> LOCATION: (6)..(6)
<223> OTHER INFORMATION: Xaa=Lys, Ser or Thr
<221> NAME/KEY: MISC_FEATURE
<222> LOCATION: (7)..(7)
<223> OTHER INFORMATION: Xaa=Ile or Val
<221> NAME/KEY: MISC_FEATURE
<222> LOCATION: (10)..(10)
<223> OTHER INFORMATION: Xaa=Ala or Pro
<221> NAME/KEY: MISC_FEATURE
<222> LOCATION: (13)..(13)
<223> OTHER INFORMATION: Xaa=Ala or Val
<221> NAME/KEY: MISC_FEATURE
<222> LOCATION: (18)..(18)
<223> OTHER INFORMATION: Xaa=Ser or Asn

<400> SEQUENCE: 1

Asn Ser Val Asn Ser Xaa Xaa Pro Lys Xaa Cys Cys Xaa Pro Thr Glx
1               5                   10                  15

Leu Xaa Ala Ile
            20

<210> SEQ ID NO 2
<211> LENGTH: 21
<212> TYPE: PRT
<213> ORGANISM: Artificial Sequence
<220> FEATURE:
<223> OTHER INFORMATION: Synthesized peptide
<221> NAME/KEY: MISC_FEATURE
<222> LOCATION: (6)..(6)
<223> OTHER INFORMATION: Xaa=Lys, Ser or Thr
<221> NAME/KEY: MISC_FEATURE
<222> LOCATION: (7)..(7)
<223> OTHER INFORMATION: Xaa=Ile or Val
<221> NAME/KEY: MISC_FEATURE
<222> LOCATION: (10)..(10)
<223> OTHER INFORMATION: Xaa=Ala or Pro
<221> NAME/KEY: MISC_FEATURE
```

```
<222> LOCATION: (13)..(13)
<223> OTHER INFORMATION: Xaa=Ala or Val
<221> NAME/KEY: MISC_FEATURE
<222> LOCATION: (18)..(18)
<223> OTHER INFORMATION: Xaa=Ser or Asn

<400> SEQUENCE: 2

Asn Ser Val Asn Ser Xaa Xaa Pro Lys Xaa Cys Cys Xaa Pro Thr Glx
1               5                   10                  15

Leu Xaa Ala Ile Ser
            20

<210> SEQ ID NO 3
<211> LENGTH: 21
<212> TYPE: PRT
<213> ORGANISM: Artificial Sequence
<220> FEATURE:
<223> OTHER INFORMATION: Synthesized peptide
<221> NAME/KEY: MISC_FEATURE
<222> LOCATION: (7)..(7)
<223> OTHER INFORMATION: Xaa=Lys, Ser or Thr
<221> NAME/KEY: MISC_FEATURE
<222> LOCATION: (8)..(8)
<223> OTHER INFORMATION: Xaa=Ile or Val
<221> NAME/KEY: MISC_FEATURE
<222> LOCATION: (11)..(11)
<223> OTHER INFORMATION: Xaa=Ala or Pro
<221> NAME/KEY: MISC_FEATURE
<222> LOCATION: (14)..(14)
<223> OTHER INFORMATION: Xaa=Ala or Val
<221> NAME/KEY: MISC_FEATURE
<222> LOCATION: (19)..(19)
<223> OTHER INFORMATION: Xaa=Ser or Asn

<400> SEQUENCE: 3

Asn Ser Val Asn Pro Glu Xaa Xaa Pro Lys Xaa Cys Cys Xaa Pro Thr
1               5                   10                  15

Glx Leu Xaa Ala Ile
            20

<210> SEQ ID NO 4
<211> LENGTH: 22
<212> TYPE: PRT
<213> ORGANISM: Artificial Sequence
<220> FEATURE:
<223> OTHER INFORMATION: Synthesized peptide
<221> NAME/KEY: MISC_FEATURE
<222> LOCATION: (7)..(7)
<223> OTHER INFORMATION: Xaa=Lys, Ser or Thr
<221> NAME/KEY: MISC_FEATURE
<222> LOCATION: (8)..(8)
<223> OTHER INFORMATION: Xaa=Ile or Val
<221> NAME/KEY: MISC_FEATURE
<222> LOCATION: (11)..(11)
<223> OTHER INFORMATION: Xaa=Ala or Pro
<221> NAME/KEY: MISC_FEATURE
<222> LOCATION: (14)..(14)
<223> OTHER INFORMATION: Xaa=Ala or Val
<221> NAME/KEY: MISC_FEATURE
<222> LOCATION: (19)..(19)
<223> OTHER INFORMATION: Xaa= Ser or Asn

<400> SEQUENCE: 4

Asn Ser Val Asn Pro Glu Xaa Xaa Pro Lys Xaa Cys Cys Xaa Pro Thr
1               5                   10                  15

Glx Leu Xaa Ala Ile Ser
            20

<210> SEQ ID NO 5
<211> LENGTH: 18
```

```
<212> TYPE: PRT
<213> ORGANISM: Artificial Sequence
<220> FEATURE:
<223> OTHER INFORMATION: Synthesized peptide
<221> NAME/KEY: MISC_FEATURE
<222> LOCATION: (4)..(4)
<223> OTHER INFORMATION: Xaa=Lys, Ser or Thr
<221> NAME/KEY: MISC_FEATURE
<222> LOCATION: (5)..(5)
<223> OTHER INFORMATION: Xaa=Ile or Val
<221> NAME/KEY: MISC_FEATURE
<222> LOCATION: (8)..(8)
<223> OTHER INFORMATION: Xaa=Ala or Pro
<221> NAME/KEY: MISC_FEATURE
<222> LOCATION: (11)..(11)
<223> OTHER INFORMATION: Xaa=Ala or Val
<221> NAME/KEY: MISC_FEATURE
<222> LOCATION: (16)..(16)
<223> OTHER INFORMATION: Xaa=Ser or Asn

<400> SEQUENCE: 5

Ile Asn Ser Xaa Xaa Pro Lys Xaa Cys Cys Xaa Pro Thr Glx Leu Xaa
1               5                   10                  15

Ala Ile

<210> SEQ ID NO 6
<211> LENGTH: 19
<212> TYPE: PRT
<213> ORGANISM: Artificial Sequence
<220> FEATURE:
<223> OTHER INFORMATION: Synthesized peptide
<221> NAME/KEY: MISC_FEATURE
<222> LOCATION: (4)..(4)
<223> OTHER INFORMATION: Xaa=Lys, Ser or Thr
<221> NAME/KEY: MISC_FEATURE
<222> LOCATION: (5)..(5)
<223> OTHER INFORMATION: Xaa=Ile or Val
<221> NAME/KEY: MISC_FEATURE
<222> LOCATION: (8)..(8)
<223> OTHER INFORMATION: Xaa=Ala or Pro
<221> NAME/KEY: MISC_FEATURE
<222> LOCATION: (11)..(11)
<223> OTHER INFORMATION: Xaa=Ala or Val
<221> NAME/KEY: MISC_FEATURE
<222> LOCATION: (16)..(16)
<223> OTHER INFORMATION: Xaa=Ser or Asn

<400> SEQUENCE: 6

Ile Asn Ser Xaa Xaa Pro Lys Xaa Cys Cys Xaa Pro Thr Glx Leu Xaa
1               5                   10                  15

Ala Ile Ser

<210> SEQ ID NO 7
<211> LENGTH: 19
<212> TYPE: PRT
<213> ORGANISM: Artificial Sequence
<220> FEATURE:
<223> OTHER INFORMATION: Synthesized peptide
<221> NAME/KEY: MISC_FEATURE
<222> LOCATION: (5)..(5)
<223> OTHER INFORMATION: Xaa=Lys, Ser or Thr
<221> NAME/KEY: MISC_FEATURE
<222> LOCATION: (6)..(6)
<223> OTHER INFORMATION: Xaa=Ile or Val
<221> NAME/KEY: MISC_FEATURE
<222> LOCATION: (9)..(9)
<223> OTHER INFORMATION: Xaa=Ala or Pro
<221> NAME/KEY: MISC_FEATURE
<222> LOCATION: (12)..(12)
<223> OTHER INFORMATION: Xaa=Ala or Val
<221> NAME/KEY: MISC_FEATURE
<222> LOCATION: (17)..(17)
<223> OTHER INFORMATION: Xaa=Ser or Asn
```

<400> SEQUENCE: 7

Ile Asn Pro Glu Xaa Xaa Pro Lys Xaa Cys Cys Xaa Pro Thr Glx Leu
1               5                   10                  15

Xaa Ala Ile

<210> SEQ ID NO 8
<211> LENGTH: 20
<212> TYPE: PRT
<213> ORGANISM: Artificial Sequence
<220> FEATURE:
<223> OTHER INFORMATION: Synthesized peptide
<221> NAME/KEY: MISC_FEATURE
<222> LOCATION: (5)..(5)
<223> OTHER INFORMATION: Xaa=Lys, Ser or Thr
<221> NAME/KEY: MISC_FEATURE
<222> LOCATION: (6)..(6)
<223> OTHER INFORMATION: Xaa=Ile or Val
<221> NAME/KEY: MISC_FEATURE
<222> LOCATION: (9)..(9)
<223> OTHER INFORMATION: Xaa=Ala or Pro
<221> NAME/KEY: MISC_FEATURE
<222> LOCATION: (12)..(12)
<223> OTHER INFORMATION: Xaa=Ala or Val
<221> NAME/KEY: MISC_FEATURE
<222> LOCATION: (17)..(17)
<223> OTHER INFORMATION: Xaa=Ser or Asn

<400> SEQUENCE: 8

Ile Asn Pro Glu Xaa Xaa Pro Lys Xaa Cys Cys Xaa Pro Thr Glx Leu
1               5                   10                  15

Xaa Ala Ile Ser
            20

<210> SEQ ID NO 9
<211> LENGTH: 20
<212> TYPE: PRT
<213> ORGANISM: Artificial Sequence
<220> FEATURE:
<223> OTHER INFORMATION: Synthesized peptide

<400> SEQUENCE: 9

Asn Ser Val Asn Ser Lys Ile Pro Lys Ala Cys Cys Val Pro Thr Glu
1               5                   10                  15

Leu Ser Ala Ile
            20

<210> SEQ ID NO 10
<211> LENGTH: 20
<212> TYPE: PRT
<213> ORGANISM: Artificial Sequence
<220> FEATURE:
<223> OTHER INFORMATION: Synthesized peptide

<400> SEQUENCE: 10

Asn Ser Val Asn Ser Ser Ile Pro Lys Ala Cys Cys Val Pro Thr Glu
1               5                   10                  15

Leu Ser Ala Ile
            20

<210> SEQ ID NO 11
<211> LENGTH: 20
<212> TYPE: PRT
<213> ORGANISM: Artificial Sequence
<220> FEATURE:
<223> OTHER INFORMATION: :

-continued

```
<400> SEQUENCE: 11

Ile Asn Pro Glu Thr Val Pro Lys Pro Cys Cys Ala Pro Thr Gln Leu
1               5                   10                  15

Asn Ala Ile Ser
            20
```